(12) United States Patent
Vaughnn (10) Patent No.: US 8,204,298 B2
(45) Date of Patent: Jun. 19, 2012

(54) FOCUSING METHOD AND APPARATUS (75) Inventor: David Vaughnn, Edina, MN (US)

(73) Assignee: Rudolph Technologies, Inc., Flanders, NJ (US)

(*) Notice: Subject to any disclaimer, the term of this patent is extended or adjusted under 35 U.S.C. 154(b) by 0 days.

(21) Appl. No.: 13/180,080

(22) Filed: Jul. 11, 2011

(65) Prior Publication Data
US 2011/0268348 A1 Nov. 3, 2011

Related U.S. Application Data (63) Continuation of application No. 11/781,047, filed on Jul. 20, 2007, now abandoned.

(60) Provisional application No. 60/832,196, filed on Jul. 20, 2006.

(51) Int. Cl.
G06K 9/00 (2006.01)
H04N 5/232 (2006.01)
(52) U.S. Cl. .......................... 382/151; 382/318; 348/349
(58) Field of Classification Search .................. 382/151, 382/318; 348/349
See application file for complete search history.

(56) References Cited

U.S. PATENT DOCUMENTS

| 4,804,831 | A | * | 2/1989 | Baba et al. ................ 250/201.2 |
| 5,212,516 | A | * | 5/1993 | Yamada et al. ............... 348/354 |
| 5,835,627 | A | * | 11/1998 | Higgins et al. ............... 382/167 |
| 5,903,662 | A | | 5/1999 | DeCarlo |
| 6,363,168 | B1 | | 3/2002 | Kakuma |
| 2005/0280735 | A1 | * | 12/2005 | Nakahara ..................... 348/345 |
| 2006/0239507 | A1 | | 10/2006 | Schenck |

* cited by examiner

Primary Examiner — Kathleen Y Dulaney
(74) Attorney, Agent, or Firm — Dicke, Billig & Czaja, PLLC (57) ABSTRACT Methods and apparatus for placing wafers axially in an optical inspection system. A "best worst" focus method includes a series of through-focus images of a test wafer acquired using full field of view of the inspection optics. The value of the worst quality in each image is associated with the respective axial location, forming a locus of "worst" values as a function of axial location. The axial location is chosen which optimizes the locus, giving an axial location that provides the "best-worst" image quality. A "video focus" method includes a series of through-focus images generated using reduced field of view. A figure of merit is associated with each image, providing through-focus information. The "video focus" can be calibrated against the "best worst" focus. Further, a point sensor can be used to generate a single z-value for one (x,y) location that can be calibrated with "video focus".

15 Claims, 5 Drawing Sheets

FOCUSING METHOD AND APPARATUS

CROSS-REFERENCE TO RELATED APPLICATIONS

This application is a continuation of U.S. patent application Ser. No. 11/781,047, filed Jul. 20, 2007, entitled "Focusing Method and Apparatus", and claims priority under 35 U.S.C. §119(e)(1) to U.S. Provisional Patent Application Ser. No. 60/832,196, filed Jul. 20, 2006, entitled "Method of Designing Optical Systems,"; the teachings of which are hereby incorporated by reference.

TECHNICAL FIELD

The present invention relates generally to a focusing technique for visual inspection systems.

BACKGROUND

In a typical visual inspection system for semiconductor wafers, all or a portion of a wafer is imaged onto a camera. The image captured by the camera is typically processed by software to determine the presence, absence, size and/or orientation of one or more particular features on the wafer. The particular features may vary, depending on the particular application of the inspection system. As used herein, the term "wafer" is to be construed to be inclusive of at least the following: an entire semiconductor wafer, a portion of a single die formed on a semiconductor wafer, a single die formed on a semiconductor wafer, multiple die formed on a semiconductor wafer, and portions or pieces of an entire semiconductor wafer (broken or sawn). The term "wafer" may also be construed as any substrate suitable for visual inspection. Further, the term "visual inspection" shall be construed to include any process or apparatus that involves the focusing of electromagnetic radiation of any wavelength at a given focal point or plane.

In general, it is desirable that the wafers be inspected quickly, so that a relatively large number of wafers may be inspected in a relatively short amount of time. There is continual effort to improve the efficiency of the inspection system algorithms and reduce the time required to inspect each wafer.

One step in a typical inspection system algorithm involves axially placing each wafer at the desired imaging plane, with respect to the imaging optics. Once the wafer is placed, the optics image the wafer or a portion of the wafer. In general, this axial location helps determine the quality of the image captured by the camera. It is a continual challenge to balance high throughput of the wafers through the inspection system (speed) versus accurate placement of each wafer at the most desirable imaging plane (accuracy).

Accordingly, there exists a need for increased efficiency in ensuring that each wafer is placed at a desired imaging plane, with respect to the imaging optics.

SUMMARY

One embodiment of a method of determining a desired axial location for placement of an imageable object in an inspection optical system, involves placing an axially-translatable object within a field of view of the inspection optical system; axially translating the object sequentially to a plurality of axial locations; acquiring a plurality of images of the translated object, each of the plurality of images being associated with a respective axial location; determining a plurality of lateral-location-dependent figures of merit for the plurality of mages, each of the plurality of lateral-location-dependent figures of merit being associated with a respective axial location; identifying a plurality of worst image quality values from the plurality of lateral-location-dependent figures of merit, each of the plurality of worst image quality values being associated with a respective axial location; determining a best worst image quality value from the plurality of worst image quality values; associating the best worst image quality value with a desired axial location, based on the associations between the worst image quality values and the axial locations; and selecting the desired axial location.

Another embodiment concerns a method of calibrating an optical inspection system, which may involve calculating a "best worst" axial position for a first objective lens using a full field of view of the first objective lens; acquiring a series of through-focus images using a reduced field of view of the first objective lens; and calibrating the series of through-focus images to the "best worst" axial position.

A further embodiment is a method of inspecting a substrate that may include determining a "best worst" axial location; acquiring a series of reduced-field-of-view, through-focus images of a substrate; correlating the reduced-field-of-view, through-focus images to the "best worst" axial location; and placing the substrate at the "best worst" axial location.

DETAILED DESCRIPTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

Figure 1:
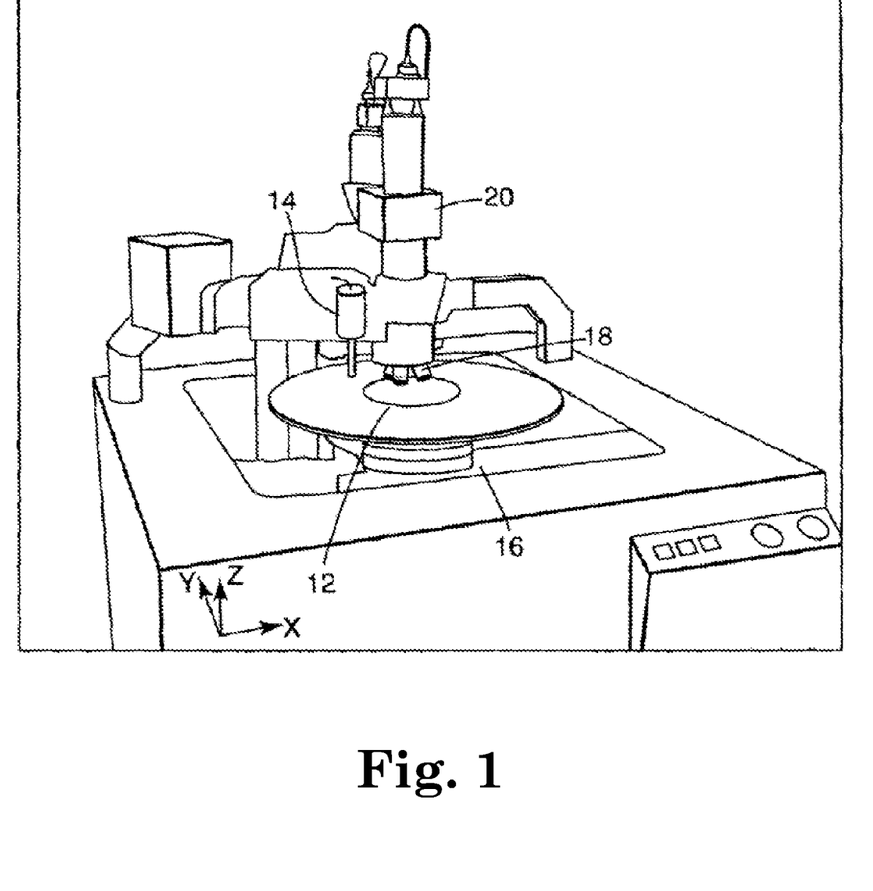
FIG. 1 is a perspective drawing of an exemplary inspection system.

An exemplary inspection system is illustrated in FIG. 1. The inspection system may include an optical sensor or camera 20, one or more selectable focusing mechanisms 18, such as objectives or lenses, an auxiliary sensor 14, and an inspection platform 12 coupled to a wafer alignment device 16 for moving the platform 12 relative to the camera 20.

The inspection platform 12 is in some embodiments a rotary stage that may be equipped with a universal interface platform with vacuum to provide a flexible interface for wafer and die package fixturing. The platform 12 is defined such that it quickly mounts and inspects substrates such as whole wafers, portions of wafers, sawn wafers on film frame, die in gel pak, die in waffle-pak, MCM, JEDEC trays, Auer boats, and other wafer and die package arrangements and configurations. Note that as used herein, the term "wafer" may be used interchangeably with the term "substrate" and/or with any of the alternative items named in the preceding sentence, among others.

The wafer alignment device 16, which aligns each and every wafer at the same x, y, z, and θ location, may be a precision system of rotary motors, ball screws, direct or belt driven motors, worm or other gears, actuators, hydraulics, push rods, vacuums, or other mechanical or electrical equipment for moving the rotary stage either linearly or angularly to a precise desired location.

The focusing mechanism 18 may be an optical imaging mechanism with multiple optics therein for using different inspection resolutions. A motorized microscopic turret allows for selecting of the imaging optics from the multiple choices. For instance, a number of optics, such as three or five optics, may be supplied and typical choices include 1.25×, 2.5×, 5×, 10×, 20×, 50× and 100× objectives. The motorized microscopic turret and discrete objectives provide the means to select the optical magnification.

The camera system 20 or other visual inspection device is for visual inspection of wafers and/or die and portions thereof. The camera system may be any type of camera capable of high resolution inspection. An example of one part of such a camera system is a 3-CCD inspection camera used to capture die or other images during defect analysis.

Focusing of the camera 20 is accomplished by facilitating relative movement between a wafer positioned on inspection platform 12 and the camera 20. Relative motion between the inspection platform 12 and the camera system 20 is along an axis defined by the optical axis of the camera system 20, commonly designated the "z" axis (the "x" and "y" axes commonly being arranged in the plane of a wafer on the inspection platform 12). Relative motion between the camera 20 and the inspection platform 12 is achieved by moving the wafer alignment device 16 (to which is mounted the inspection platform 12) with respect to the camera 20, the camera 20 with respect to the inspection platform 12, or both, the one with respect to the other.

It is instructive to provide a simplistic example of the issues that affect the axial placement of each wafer with respect to the optics in the inspection system. This simplistic example is intended merely to clarify these issues, and should not be construed as in any way limiting the scope of the present disclosure.

Figure 2:
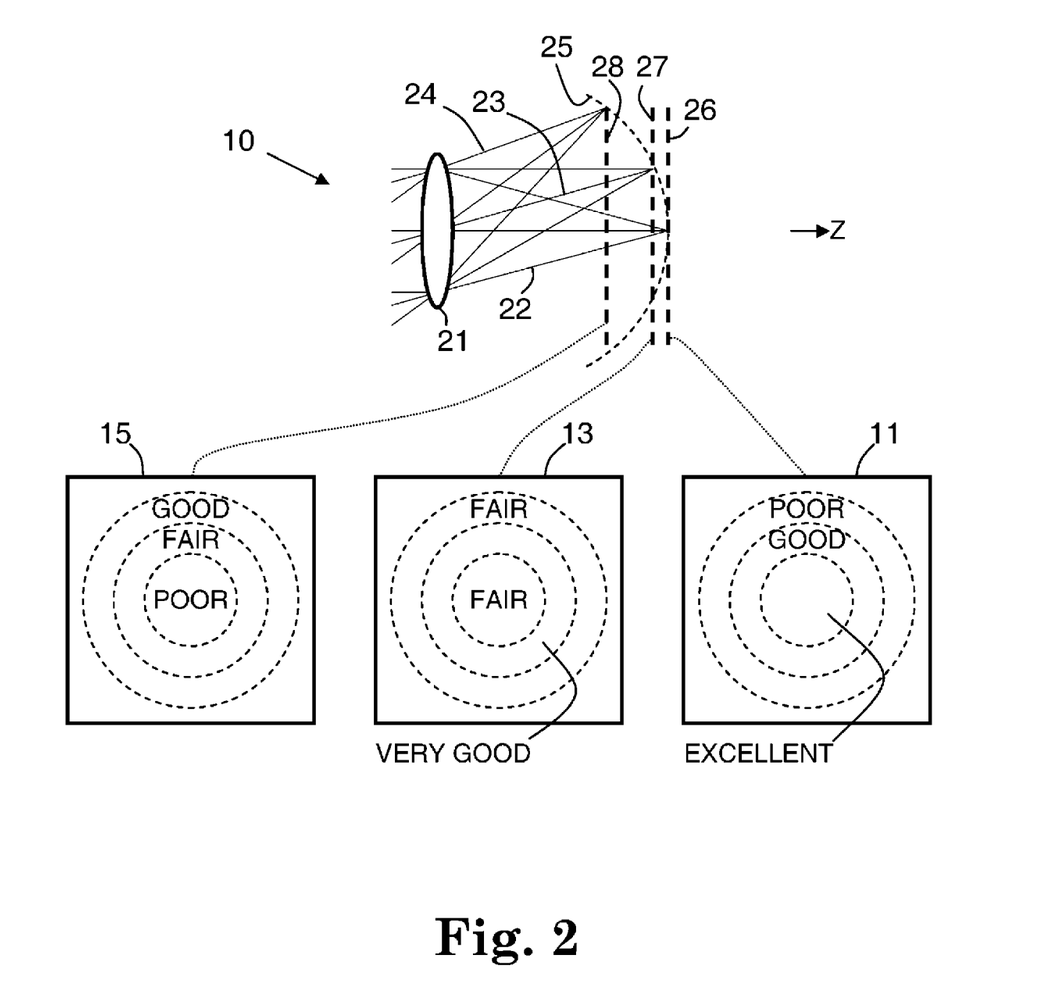
FIG. 2 is a schematic drawing of an exemplary optical system having field curvature, with three exemplary through-focus image quality maps.

FIG. 2 is a schematic drawing of the image quality at three different through-focus planes, for a generic inspection system 10 in which the optics have a finite field curvature. This is a simplified example; in practice, the optics may have other aberrations in addition to field curvature, but the case of simple field curvature is sufficiently illustrative for this example.

The optics 21 of the inspection system 10 are exemplified as a simple single-element lens in FIG. 2, but may include any or all of a light source, a fiber, a beam homogenizer, a waveplate, a beamsplitter, a collimator lens, a camera, a detector and/or an objective lens. Light emerges from the optics 21 and comes to a focus, preferably at or near the wafer to be inspected. Light reflects off the wafer (not shown) and returns through the optics 21 to a camera (not shown) or other imaging device that produces an image of the wafer under inspection. The illumination optical system may operate in bright field and/or in dark field, and the collection optical system may also operate in bright field and/or in dark field.

The optics 21 in this example have a finite field curvature, so that rays 22 near the center of the field of view come to focus at a particular plane 26, rays 23 away from the center of the field of view come to focus at a plane 27 closer to the optics 21 than plane 26, and rays 24 near the edge of the field of view come to focus at a plane 28 still closer to the optics 21 than either plane 26 or plane 27. The locus of these foci forms a curved field 25. In practice, the field 25 may have a much more complex shape than a sphere or a paraboloid, but this simple shape of the curved field 25 is sufficient to show the issues associated with axial positioning of the wafer.

Planes 26, 27 and 28 represent potential axial positions at which the wafer may be placed for inspection. Elements 11, 13 and 15 are graphic representations of the image quality at planes 26, 27 and 28, respectively, and may be referred to as image quality maps.

The notations in FIG. 2 of "excellent", "very good", "good", "fair" and "poor" may correspond to a figure of merit suitable for inspection systems, such as RMS spot size, RMS wavefront error, edge transition width, encircled energy, Modulation Transfer Function (MTF), Strehl Ratio, or any other suitable single-valued figure of merit. The precise correlation between these terms and numerical values is unimportant for the simplistic example of FIG. 2, but we may generalize that an "excellent" location in the image (or, equivalently, in the field of view) has a smaller RMS spot size, or a higher Strehl Ratio, etc., than a "very good" location, and so forth. The notations should be interpreted literally, in that "poor" may not truly be unacceptable, and so forth; these notations exist only for relative comparison.

For image 11, at plane 26, the center of the image may have "excellent" quality, so that features in this central portion are clearly represented in the image. Away from this central portion, the image quality erodes, becoming "good" and then "poor" at the edge of the field of view. Features near the edge of the field of view may be blurred or poorly resolved.

For image 13, at plane 27, the central portion of the image may have "fair" quality. The portion surrounding the center may have "very good" image quality, and the edge of the image may also have "fair" quality.

For image 15, at plane 28, the central portion of the image may have "poor" quality, the portion surrounding the center may have "fair" image quality, and the edge of the image may have "good" quality.

Note also that the image quality maps 11, 13 and 15 are determined only by the optics 21 of the inspection system 10, and are not affected by the wafers that are to be inspected. These image quality maps generally do not vary significantly over time unless changes are made to the inspection system optics.

Based in part on the image quality maps or on other analysis of the image quality, the inspection system designer and/or operator decides at which plane the wafers under inspection should be placed. For instance, if it is decided that the wafers should be located at plane 26, then for each captured image of a wafer, the center of the field of view may look "better" than the edge of the field of view. Similarly, if it is decided that the wafers should be located at plane 28, then the edge of the field of view may look "better" than the center.

Once a decision is made as to which plane the wafers should be placed, it becomes an engineering challenge to repeatably place each wafer at the chosen plane, to do it within a certain positional tolerance and to do it quickly. Accordingly, much attention is devoted in the following paragraphs to these issues. First, the text describes a scheme for determining at which plane the wafer should be placed. Following that, the text describes a scheme for placing the wafer at the desired plane.

The following paragraphs describe a scheme for determining at which plane the wafer under inspection should be placed, which may be referred to as the "best worst" scheme.

For each of the three axial positions (or, equivalently, focus positions), shown in image quality maps 11, 13 and 15, certain portions of the image (or, equivalent, the field of view) may have higher quality than other portions. For each axial position 26, 27 and 28, one may find the "worst" portion of each image. For instance, for position 26, the "worst" portion may be in the corners of the image. For position 27, the "worst" portion may be either in the center or in the corners. For position 28, the "worst" portion may be in the center of the image. In general, for any and all of the axial positions, there exists a value for the "worst" quality in the image.

A preferable axial position is at or near the point at which this "worst" quality in the image is optimized—literally the "best-worst" point. For the simplistic example of FIG. 2, a preferable axial position may be position 27, at which the worst quality anywhere in the image is merely "fair"; on either side of position 27, at positions 26 and 28, the worst quality anywhere in the image is "poor".

Figure 3:
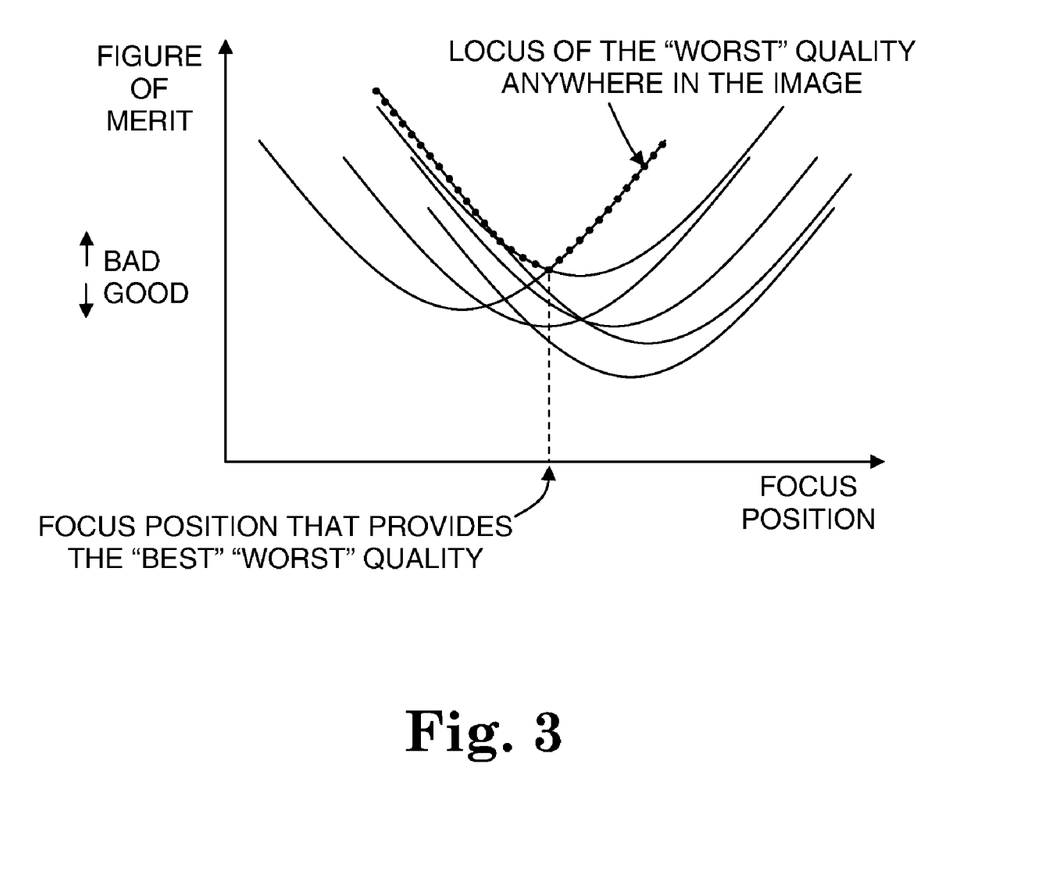
FIG. 3 is an exemplary plot of through-focus image quality, and the locus of "worst" image quality.

FIG. 3 is an exemplary plot of "quality" versus focus position, for all the locations in an image. Each curve represents a particular location in the field of view, such as a pixel or group of pixels. Each curve has its own local minimum (or maximum, depending on the figure of merit), but the local minima (or maxima) for all the curves do not necessarily lie at the same axial location.

From these curves, one may form a locus of the "worst" quality anywhere in the image, for a particular focus position. Graphically, this locus may be obtained by examining a vertical slice of the curves and using the maximum (or minimum, depending on the figure of merit) value in the slice as a point in the locus.

Once the locus of the "worst" quality is formed, one may find the minimum value of the locus, which is literally the "best" value of the locus of "worst" values. The focus position that provides this "best worst" value is the desired focus position. In other words, it is desirable that each wafer to be inspected be placed at or near this "best worst" focus position.

Note that "quality", as used in the plot of FIG. 3, may refer to any suitable single-valued figure of merit, such as RMS or peak-to-valley spot size, RMS or peak-to-valley wavefront error, Strehl Ratio, MTF at a particular spatial frequency, edge transition width, and so forth. Note that this figure of merit may correspond to the low-number-is-good condition shown in FIG. 3, as is the case for spot size, wavefront error, edge transition width, and so forth. Alternatively, the figure of merit may correspond to a high-number-is-good condition, such as Strehl Ratio or MTF, in which case the y-axis in FIG. 3 would be inverted. It is desirable to use a figure of merit that may be measured, and even more desirable to use a figure of merit that may be measured using the actual optics of the inspection system and a test wafer. For this reason, the edge transition width is a particularly desirable figure of merit, which can be measured directly by the inspection system when light reflected from a test wafer having sufficiently small features is collected and detected by the camera/imaging optics.

Note also that the curves in FIG. 3 may be much more numerous in practice. For instance, if a detector or camera has a sensor configuration of 640 pixels by 480 pixels, the number of curves may be as large as 307,200. In practice, the point on the "worst" locus corresponding to a given axial location is found by taking the value of the "worst" image quality of these 307,200 pixels.

In addition, the actual curves may have much more complex shapes than those in FIG. 3. Depending on the optical system, the curves may have local maxima or minima, or may curve more steeply on one side than the other.

In practice, the precise number and shape of the curves are relatively unimportant. The point on the locus of "worst" quality may be found for each focus location by selecting the "worst" value of image quality for each image's pixels or subgroup of pixels, and the "best" value on this locus provides the desired axial location for the wafer to be inspected.

Note that the images are taken at discrete planes, through-focus. The "worst" value of image quality may be interpolated between these discrete planes to form a continuous function. In this manner, the "best-worst" value may be associated with a plane that is not necessarily one of the planes at which the images are taken.

Note that the focus position shown in FIG. 3 and described above is typically fairly close to the position at which the "quality" variation (best-to-worst, or peak-to-valley) is minimized. In many camera-based inspection systems, it is desirable to minimize or reduce the variation in quality across the field-of-view, rather than optimize one location in the field at the expense of another location in the field. In other words, it may be acceptable in many inspection applications to have a slightly degraded image, as long as the degradation is roughly uniform over the field-of-view. The variation in such a degradation across the field of view may be sufficiently reduced at or near the "best worst" focus position described above.

In some embodiments, it is desirable that the axial placement of the wafer be within the depth of focus of the imaging system. The depth of focus may be defined in several ways, such as an axial displacement that degrades the image by a particular amount. This degradation due to defocus may be an increase in RMS spot size by a particular percentage such as 10%, or an increase in the RMS wavefront error to a particular threshold such as 0.07 waves, or a decrease in the Strehl Ratio to a particular threshold such as 80%. In some embodiments, the depth of focus may depend linearly on the central wavelength of the illuminating light, and may depend inversely as the numerical aperture of the collection optics, squared.

The "best worst" focus condition described above may be found experimentally, by stepping a test wafer through focus, and acquiring and processing the through-focus images of the test wafer. Note that this "best worst" focus condition does not depend on the wafer under inspection, but depends only on the illumination, collection and/or imaging optics in the inspection system. For instance, if the "best worst" focus condition in a particular system is such that the wafer should be placed 1.0 mm away from a particular feature on the objective lens, then as long as the optics remain aligned and thermally stable, the 1.0 mm criterion will hold, regardless of any properties of the wafer under test. In other words, once the "best worst" focus condition is established for a given optical system, it generally need not be re-established until something in the system changes.

The preceding paragraphs describe a particular "best worst" axial position. An image of a wafer placed at the "best worst" axial position generally has a reduced variation in image quality across the field-of-view (or, equivalently, across the spatial extent of the image). It is an ongoing engineering challenge to place wafers at or near that axial position, and to place them rapidly and accurately. The following paragraphs describe several focusing methods and their use together to address this challenge.

The following paragraphs describe use of a so-called "point sensor", which is shown schematically in FIG. 1 as an "auxiliary" sensor 14. The point sensor takes data in one (x,y) location and provides z-data, which may be the distance between the point sensor and the wafer under inspection or a scaled or shifted version thereof. In some embodiments, the point sensor is a largely self-contained unit that is attached to the mechanical supports that house the camera optics. Alternatively, the point sensor may be integrated into the camera optics or into the mechanical supports themselves. The point sensor may be arranged so as to measure a z-height at an (x,y) location located within the field of view of the optics, or, alternatively, at an (x,y) location outside the field of view. Point sensors may use triangulation, confocal techniques, or any suitable technique that provides z-height data.

An advantage to using point sensors is that they operate quickly. A typical point sensor can return a z-value in about 1 millisecond, and can run in a repeat mode with a frequency on the order of 1 kHz. The response of a point sensor may be fast enough to produce measurements on moving wafers, as the wafers are translated past the (relatively stationary) point sensor location by the handling robotics of the inspection system.

For instance, a point sensor may be used to measure a global object position (analogous to measuring piston error in an interferometer) by making a z-measurement at the center of the wafer under inspection. The point sensor may make a tip-tilt measurement by measuring z at 4 or 5 points along the circumference (and optionally the center) of the wafer (analogous to measuring tilt in an interferometer). Furthermore, the point sensor may map out a focus map of the wafer by taking z measurements in a loose grid along the wafer surface (analogous to measuring low-order aberrations in an interferometer).

For all of the above measurements, the point sensor typically remains fixed or stationary, and the wafer is typically translated and/or rotated past the (x,y) measurement spot. Alternatively, the wafer may remain relatively stationary while the point sensor moves, or both the point sensor and the wafer may move.

In addition, a point sensor may operate with a featureless wafer. Because no wafer features are needed to produce a z-measurement, there is no need to use a test wafer with a point sensor.

Despite the numerous advantages of using a point sensor, a point sensor alone is generally insufficient to fully inspect a wafer, and a camera or imaging system is typically used in conjunction with the point sensor. Because the point sensor and imaging optics may be in separate mechanical housings, there may be a small amount of z-drift over time between the point sensor and the imaging optics. The effect of this drift may be that when the point sensor z-measurement indicates that a wafer is in the desired plane for high-quality imaging, the wafer may actually be axially displaced away from the desired plane by the amount of the drift. This z-drift may be caused by temperature changes, excessive building vibration or any other perturbing feature from the environment.

In order to correct for the drift between the point sensor and the camera or imaging optics, a calibration may be done using a series of through-focus images of the wafer, taken by the camera or imaging optics. This calibration may be referred to as "video focus".

The through-focus images may use a limited portion of the full field of view, such as the central portion, so that they may be acquired and processed more quickly. The term "video focus field of view" may be used to refer to the limited field of view, and the term "inspection field of view" may be used to refer to the full field of view.

Each of the through-focus images may be processed by a so-called "fast" algorithm that can find a desirable focus. For instance, an algorithm that measures the (point-by-point) contrast of an image may be used on each of the through-focus images, with the most desirable focus occurring at the z-location where contrast is maximized. Similarly, an algorithm using the edge transition width may also be used, with the most desirable focus occurring when the edge transition width is minimized. Many of these algorithms require one or more features on the wafer, so that if an inspection system is configured to test only featureless wafers, a test wafer should be used for "video focus". The test wafer may be stored in or with the inspection system. The test wafer may have one or more imageable features on it, such as a line, an edge, a corner, a point, an interface, a fiducial mark or index, and so forth.

Despite being referred to as "fast", the so-called "fast" algorithm still takes significantly longer to perform than a measurement from a point sensor. With current computing power, a typically video focus procedure (acquiring and processing a series of reduced-field-of-view images through focus) may take on the order of 3 seconds.

The "video focus" procedure may be used to calibrate the z-drift between the point sensor and the imaging optics as follows. A "video focus" procedure is run on a particular feature on a wafer, producing a series of through-focus images, each image associated with a particular z-location. An algorithm is applied to the images, sensing contrast, edge transition width or any other suitable metric. The algorithm images generate the metric as a function of z-location, and a desired z-location is chosen based on the metric having a maximum value, a minimum value, a predetermined value, or entering a particular range of values. The particular feature is then translated and/or rotated to lie at or near the (x,y) location of the point sensor, if required. The point sensor produces its own value of z-location of the wafer at the particular feature. The z-locations of the video focus and point sensor may then be compared, with a difference in reported z-values corresponding to a drift between the point sensor and the imaging optics. Alternatively, the point sensor procedure may be performed before the video focus procedure.

Ultimately, the calibration procedure between the video focus and point sensor ensures that drift between the point sensor and the imaging optics is accounted for. In this manner, the point sensor may be used (either in a closed-loop feedback loop or in open-loop) to quickly move a particular wafer under inspection to the proper axial location.

Acquiring the readings from the point sensor to find the proper axial location for the wafer is practically instantaneous, requiring only about 1 millisecond per measurement. Many point sensor measurements may be taken as needed as the wafer under inspection is moved into the desired axial location. When a point sensor is used, the positioning of the wafer at the desired axial location is limited only by the speed of the positional system in the inspection system. In contrast, if only the video focus is used to find the proper axial location, it may take about 3 seconds per lateral location on a wafer, which is significantly slower.

This calibration between the point sensor and the video focus may be performed at periodic intervals, such as once an hour, or any other suitable regular or irregular interval. Running a 3-second-long procedure once an hour is certainly preferable to running the 3-second-long procedure for every lateral location on each wafer under inspection.

Note that the desired axial location for the wafer may satisfy the "best worst" condition described above, or may be any suitable axial location.

Once the wafer is brought to the desired axial location, a full-field-of-view image is taken, which may be then processed and analyzed for inspection. Note that the full-fieldof-view image may be taken using the same optical system as the video focus, where the video focus uses a reduced field-of-view.

It is worth noting that the "video focus", which uses a reduced field of view, may optionally include an axial offset with respect to the "best worst", which uses the full field of view. For instance, if the "video focus" uses only the center of the field of view, and the optical system has the characteristics shown in FIG. 2, then the "video focus" used without an axial offset may erroneously indicate that plane 11 is the most suitable plane for the wafers, rather than plane 13. In other words, the "video focus" may not be sensitive to effects outside its limited field of view. Because of this, there may be a calibrated axial offset built into the "video focus" routine, which can account for effects that lie outside the limited field of view. This predetermined axial offset may be set up during construction of the optical system, or may be manually adjustable by an operator.

It is worth noting that the axial placement of an object typically has a tolerance associated with it, which depends on the mechanical positioning element(s) in the inspection system. The tolerance may vary with the specific application, and may optionally vary with the desired magnification of the optical system. In general, placement "at" a particular plane may refer to placement at the plane to within the tolerance.

It is instructive to compare several of the focus methods described above to each other, in terms of the frequency at what they may be performed and the duration of such a technique.

The "best worst" technique may be performed quite infrequently, since there is essentially no drift between the "best worst" optics and the "video focus" optics; they both use the identical optical path. Finding the "best worst" axial position (or, equivalently, focus position) should be done once, when the optical system is first assembled. It may be done on a periodic but infrequent basis, such as once a year, if there is a noticeable degradation in the performance of the optics. For production, one would not want to perform the "best worst" technique for every wafer; such a technique may take up to four hours or more, which is unsuitable for a high-throughput production environment.

The "video focus" technique may be performed periodically in a production environment. For instance, the video focus may be performed once for a predetermined length of time, such as an hour or a week. Or, the video focus may be performed once for every few wafers inspected, such as 10 wafers, 100 wafers, or any suitable number. Alternatively, the video focus may be performed for a given number of inspections, or actual number of images taken. As a further alternative, it may be performed whenever the inspection system is bumped, such as when an accelerometer with the inspection system is triggered. In general, a video focus may be performed as needed to keep the throughput high, and may be performed to address fairly fast drift changes, such as a change in temperature or when the inspection system is powered up or down. It may be performed in production as needed, since it takes only about up to three seconds or so to run.

The "point sensor" technique may be performed for every wafer, and may be performed at multiple locations on every wafer if needed. The configuration of the point sensor measurement points may depend on resolution requirements, and may vary depending on the specific application. The time required for a point sensor measurement is minimal, on the order of about 1 millisecond.

In general, it would be desirable to use the point sensor technique exclusively to place a wafer at the desired axial location, due to the great speed of the technique. However, the point sensor will inevitably begin to drift axially away from the imaging optics. When this drift occurs, a video focus may be performed to re-establish calibration between the point sensor and the imaging optics. This re-calibration may be performed periodically or as needed, but need be performed only as often as required. Between these recalibrations, the point sensor may be used exclusively for placing wafers axially.

Figure 4:
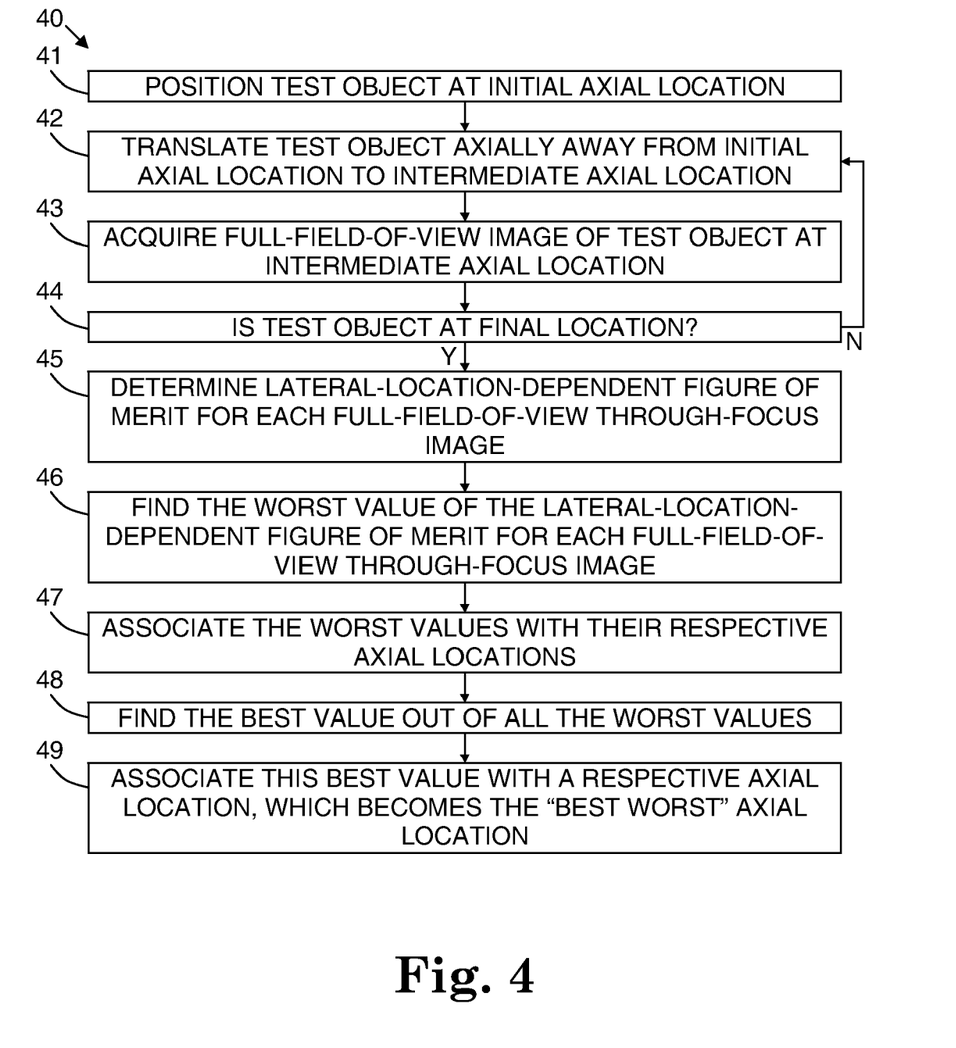
FIG. 4 is a diagram illustrating a method of identifying a "best-worst" position for a wafer.
Figure 5:
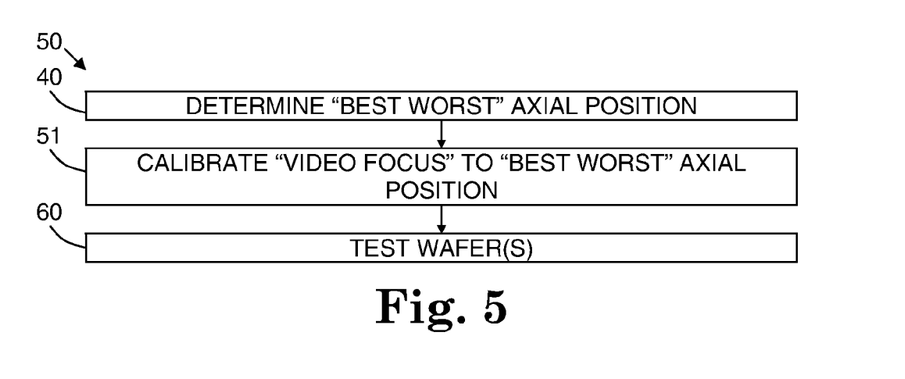
FIG. 5 is a diagram illustrating a calibration process for an optical inspection system.
Figure 6:
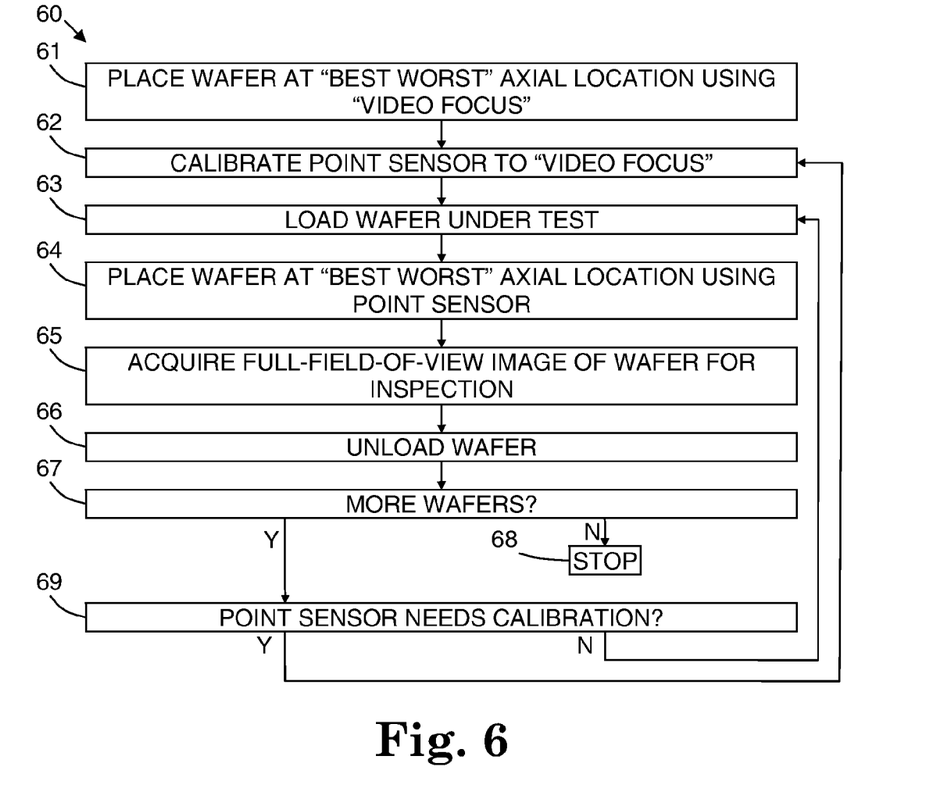
FIG. 6 is a diagram illustrating a method of a inspecting a wafer at a "best-worst" position of an optical system.

It is instructive to trace through several exemplary procedures and illustrate them in the flowcharts of FIGS. 4-6.

FIG. 4 is a flowchart of a procedure 40 to determine the "best worst" axial position.

In element 41, the test object is positioned at an initial axial location. Here the test object may be a test wafer or portion of a wafer, and may preferably include at least one feature, such as a line, and edge or a corner.

In element 42, the test object is translated axially away from the initial location to an intermediate axial location. In other words, the test object is stepped through focus. The step interval may be predetermined.

In element 43, the optical system acquires a full-field-of-view image of the test object at the intermediate axial location.

In element 44, the inspection system checks to see if the object is located at a final location, so that the initial and final axial locations surround the "best worst" axial location. The initial and final axial locations may be predetermined in an open loop fashion by simulation, or may be determined experimentally by measurements, or may be determined in an ad hoc manner during this process. If the object is not yet at the final location, elements 42 and 43 are repeated.

In element 45, for each of the images acquired in element 43, a lateral-location-dependent figure of merit is calculated. For instance, the edge transition width may be calculated for each pixel in the image, or a predetermined group of pixels in the image. Once calculated, the inspection system has values for the edge transition width (or other suitable figure of merit) as a function of (x,y) within each image, and also as a function of z for the multiple images. The figure of merit may be left as discrete values, or alternatively may be smoothed in any or all of x, y and z.

In element 46, for each image, or, equivalently, for each z-location if the z-values are smoothed, the worst figure of merit for all values of (x,y) is selected for a particular z. In element 47, this worst value is associated with the respective z-value. In this manner, elements 46 and 47 may form a locus of worst values, with a z-dependence.

In element 48, the best value may be selected from the locus of worst values.

In element 49, the z-value associated with the best value from element 48 is selected and is chosen to be the "best worst" axial location.

FIG. 5 is a flowchart of a calibration procedure 50 for an optical inspection system.

In element 40, the "best worst" axial position is determined. This is shown in greater detail in FIG. 4. Note that this procedure 40 is typically performed once, when the optical system is initially constructed, such as when an objective lens is installed or replaced. Typically, procedure 40 need not be performed with any regularity.

In element 51, the inspection system calibrates the "video focus" to the "best worst" axial position obtained from element 40. The "video focus" may use a reduced field of view, compared to the full field of view of element 43 (FIG. 4). Optionally, the "video focus" may use a relatively large field of view but may reduce the resolution or number of pixels in the images.

Once element 51 is completed, the inspection system will have a relationship between a "video focus" figure of merit and the "best worst" axial location. In this manner, the inspection system can run a "video focus", acquiring and processing a series of reduced field-of-view through-focus images. The system can then place a wafer under test at or near the "best worst" axial location based on these reduced field of view images, rather than using the full field of view of the optics, which takes more time to process.

In element 60, the inspection system can test wafers or portions of wafers. Element 60, the testing of wafers, is shown in greater detail in FIG. 6.

In general, it is desirable to use a point sensor to place wafers as much as possible, because the point sensor measurement is very fast. However, the point sensor may drift with respect to the inspection optics, due to thermal changes, vibration and so forth. Therefore, the inspection system may calibrate the point sensor to the "video focus" periodically and/or as needed. In this manner, the point sensor may be used to place wafers at or near the "best worst" axial location, until the drift significantly affects the wafer placement.

In element 61, a wafer is placed at the "best worst" axial location using "video focus". In element 62, the point sensor is calibrated to the "video focus". The point sensor may use wafers with or without features, and the "video focus" may use only wafers with features. If the inspection system is configured to test featureless wafers, then element 62 may be performed with a test wafer that has features, which may be kept in the inspection system.

A wafer under test is loaded in element 63 and is placed at the "best worst" axial location using the point sensor in element 64. Once suitably placed, the wafer is imaged in element 65, typically with the full field of view of the optics. The wafer is then unloaded in element 66.

If there are no more wafers to be tested, the system stops in element 68. If there are further wafers, the system continues.

If the point sensor needs calibration, then the system performs element 62. If no calibration is needed, element 63 is performed.

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of determining a desired axial location for placement of an imageable object in an inspection optical system defining an optical axis, comprising:
    placing an axially-translatable object within a field of view of the inspection optical system;
    axially translating the object sequentially to a plurality of axial locations along the optical axis;
    acquiring a plurality of images of the translated object, each of the plurality of images being associated with a respective axial location along the optical axis;
    determining a plurality of lateral-location-dependent figures of merit for the plurality of images using a processor, each of the plurality of lateral-location-dependent figures of merit being associated with a respective axial location along the optical axis;
    identifying a plurality of worst image quality values from the plurality of lateral-location-dependent figures of merit using the processor, each of the plurality of worst image quality values being associated with a respective axial location along the optical axis;
    determining a best worst image quality value from the plurality of worst image quality values;
    associating the best worst image quality value with a desired axial location along the optical axis, based on the associations between the worst image quality values and the axial locations along the optical axis; and
    selecting the desired axial location, wherein the desired axial location has a reduced variation in image quality across a field of view.

2. The method of claim 1, wherein each of the plurality of lateral-location-dependent figures of merit is an edge transition width.

3. The method of claim 2, wherein each of the plurality of worst image quality values is a maximum edge transition width.

4. The method of claim 1, wherein each of the plurality of lateral-location-dependent figures of merit is a contrast.

5. The method of claim 4, wherein each of the plurality of worst image quality values is a minimum contrast.

6. The method of claim 1, wherein the best worst image quality value is one of the plurality of worst image quality values.

7. The method of claim 6, wherein the desired axial location is the axial location associated with the best worst image quality value.

8. The method of claim 1, wherein the best worst image quality value is interpolated between two of the plurality of worst image quality values.

9. The method of claim 8, wherein the desired axial location is interpolated between two of the plurality of axial locations.

10. The method of claim 1, wherein the axially-translatable object has at least one imageable feature within the field of view of the inspection optical system.

11. The method of claim 1, further comprising:
    placing a second axially-translatable object within the field of view of the inspection optical system;
    defining a reduced field of view of the inspection optical system;
    axially translating the second object sequentially to a second plurality of axial locations along the optical axis;
    acquiring a second plurality of images of the second translated object, each of the second plurality of images being associated with a respective axial location along the optical axis, each image in the second plurality having the reduced field of view; and
    selecting a second axial location along the optical axis based on the second plurality of images and based on a predetermined axial offset.

12. The method of claim 11, wherein the predetermined axial offset accounts for effects within the field of view of the inspection optical system but outside the reduced field of view of the inspection optical system.

13. The method of claim 11, wherein the second axially-translatable object is different from the first axially-translatable object.

14. The method of claim 11, further comprising:
    measuring a third axial location along the optical axis of a predetermined lateral location on the second axially-translatable object with a point sensor; and
    calibrating the point sensor to account for a difference between the second and third axial locations.

15. The method of claim 1, wherein each of the plurality of lateral-location-dependent figures of merit is associated with a respective image quality value corresponding to one of the plurality of images at the respective axial location along the optical axis.

* * * * *